US011523905B2

(12) United States Patent
Griswold et al.

(10) Patent No.: US 11,523,905 B2
(45) Date of Patent: Dec. 13, 2022

(54) DEPLOYMENT RESTRAINT AND DELIVERY SYSTEM FOR IMPLANTABLE CARDIAC DEVICE

(71) Applicant: BOSTON SCIENTIFIC SCIMED, INC., Maple Grove, MN (US)

(72) Inventors: Erik Christopher Griswold, Penngrove, CA (US); Christopher Robert Lashinski, Windsor, CA (US); Randall Lashinski, Windsor, CA (US); Michael J. Lee, Santa Rosa, CA (US); Nathan D. Brown, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 238 days.

(21) Appl. No.: 16/514,061

(22) Filed: Jul. 17, 2019

(65) Prior Publication Data
US 2020/0022811 A1    Jan. 23, 2020

Related U.S. Application Data

(60) Provisional application No. 62/699,887, filed on Jul. 18, 2018.

(51) Int. Cl.
*A61F 2/24*  (2006.01)
*A61F 2/95*  (2013.01)

(52) U.S. Cl.
CPC ............ *A61F 2/2466* (2013.01); *A61F 2/246* (2013.01); *A61F 2/2445* (2013.01); *A61F 2002/9505* (2013.01); *A61F 2230/0056* (2013.01)

(58) Field of Classification Search
CPC ...... A61F 2/2466; A61F 2/2445; A61F 2/246; A61F 2002/9505; A61F 2/962; A61F 2/95; A61F 2/2436
See application file for complete search history.

(56) References Cited

U.S. PATENT DOCUMENTS 8,048,148 B2 * 11/2011 Viller ...................... A61F 2/966
                                                    623/1.35
9,180,005 B1 * 11/2015 Lashinski ............. A61F 2/2409
(Continued)

FOREIGN PATENT DOCUMENTS

WO    2008031103 A2    3/2008
WO    2017136596 A1    8/2017

OTHER PUBLICATIONS

International Search Report and Written Opinion for International application No. PCT/US2015/040622, dated Oct. 8, 2015, 9 pages.
(Continued)

*Primary Examiner* — Brian A Dukert
(74) *Attorney, Agent, or Firm* — Seager, Tufte & Wickhem LLP

(57) ABSTRACT

Features for a restraint, such as a cap, are described. The restraint secures a cardiac device in a collapsed, delivery configuration for transcatheter delivery to a heart. The restraint may have a tubular sidewall extending from a proximal end to a distal end, a proximal opening defined by the sidewall at the proximal end and a channel defined by the sidewall and extending distally from the proximal opening. The restraint is configured to receive the implant in the collapsed configuration through the proximal opening to radially restrain the implant within the channel. The restraint eliminates the need for a surrounding sheath, reducing the delivery profile and size of the overall delivery system, among other advantages. The restraint may have an atraumatic leading edge to reduce the risk of injury to the patient.

20 Claims, 11 Drawing Sheets

(56) References Cited

U.S. PATENT DOCUMENTS

| | | |
|---|---|---|
| 9,192,471 B2 | 11/2015 | Bolling |
| 9,610,156 B2 | 4/2017 | Lashinski |
| 9,615,926 B2 | 4/2017 | Lashinski et al. |
| 9,622,862 B2 | 4/2017 | Lashinski et al. |
| 9,687,373 B2 * | 6/2017 | Vad ................. A61F 2/966 |
| 9,795,480 B2 | 10/2017 | Bolling et al. |
| 9,913,706 B2 | 3/2018 | Lashinski et al. |
| 10,136,985 B2 | 11/2018 | Lashinski et al. |
| 10,321,999 B2 | 6/2019 | Glenn et al. |
| 10,335,275 B2 | 7/2019 | Lashinski et al. |
| 2014/0067037 A1 | 3/2014 | Fargahi |
| 2017/0135816 A1 | 5/2017 | Lashinski et al. |
| 2019/0241987 A1 | 8/2019 | Sohmshetty et al. |

OTHER PUBLICATIONS

International Search Report and Written Opinion for International application No. PCT/US2019/042139, dated Oct. 25, 2019, 9 pages.

* cited by examiner

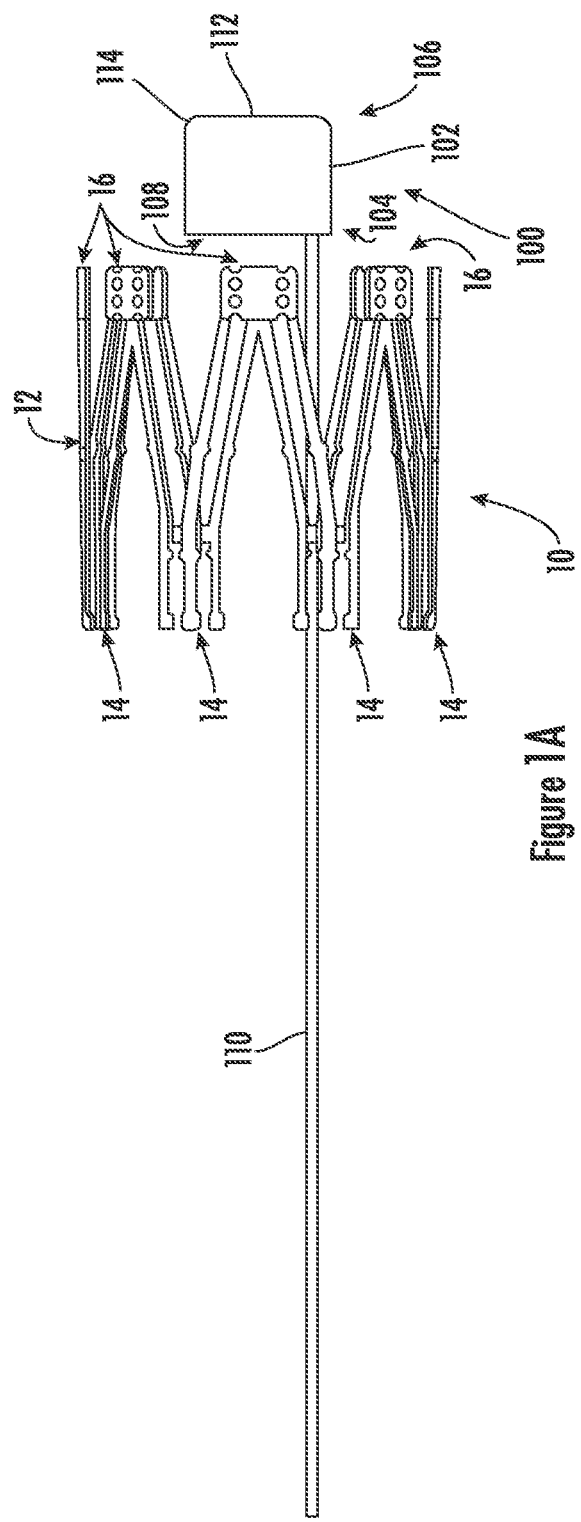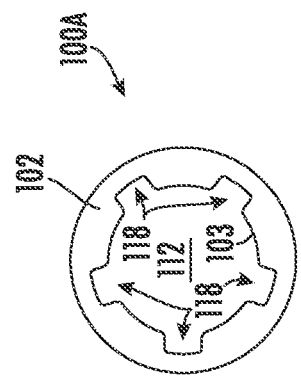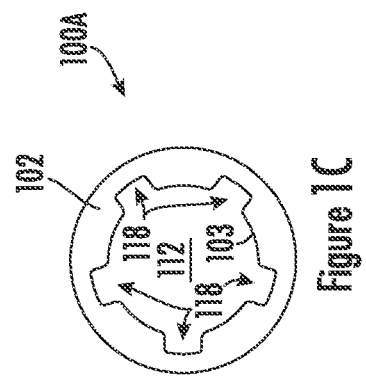

DEPLOYMENT RESTRAINT AND DELIVERY SYSTEM FOR IMPLANTABLE CARDIAC DEVICE

CROSS-REFERENCE TO RELATED APPLICATIONS

This application is a non-provisional application of, and claims the benefit of priority to, U.S. Provisional Application Ser. No. 62/699,887, filed Jul. 18, 2018, entitled "DEPLOYMENT RESTRAINT AND DELIVERY SYSTEM FOR IMPLANTABLE CARDIAC DEVICE" the entirety of which application is expressly incorporated by reference herein.

FIELD

The technology generally relates to implantable coronary medical devices. In particular, features are described for an apparatus to restrain an implant that reduces the cross sectional profile of a delivery system to enable among other things the atraumatic delivery of a medical implant through its delivery system, its channels, and the patient anatomy.

BACKGROUND

Heart valve incompetency is a serious problem. For example, heart disease can cause the chambers of the heart to expand and weaken. With specific reference to the mitral valve, as result of aging or disease, the left ventricle dilates, and the papillary muscles are displaced. Consequently, the annulus of the mitral valve dilates excessively. In this state of dilation, valve leaflets may no longer effectively close, or coapt, during systolic contraction. Consequently, regurgitation (or retrograde flow back across the valve that should be closed) of blood occurs during ventricular contraction, and cardiac output is decreased.

This condition may be addressed by the surgical implantation of an implant. This procedure is performed open chest and is time consuming. In open heart surgery, the patient is put on cardiopulmonary bypass with its associated risks of morbidity and mortality due to stroke, thrombosis, heart attack and extended recovery time.

Improvements in this field are therefore desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for delivery of cardiac implants.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

A deployment restraint is described that may be used with various implants. For example, an annuloplasty ring implant may be used to address heart valve incompetency. The implant may be delivered via transcatheter delivery. The implant may be delivered in either a minimally invasive or percutaneous manner, such as transfemorally or transeptally. The implant may be a mechanical device capable of extending out to the dilated annulus of a heart valve, engaging the tissue of the heart valve annulus, and gathering it in to a smaller diameter. The ring-like implant is typically compressed and retained in its compressed condition by the sheath for delivery to the valve site. When the sheath is withdrawn, the ring-like implant returns to an expanded diameter to engage the dilated annulus and is then reduced in size to reconfigure the valve annulus down to a smaller diameter, reducing and/or eliminating the regurgitation.

In practice, however, the combination of a delivery system, sheath and guide catheter presents a relatively larger profile with respect to the patient anatomy to which it must traverse. It would be preferable to reduce the profile of the overall system.

A deployment restraint, such as a cap, is described. The restraint mechanism disclosed herein eliminates the need for the surrounding sheath, reducing the size of the overall system, among other advantages. The restraint can also have an atraumatic leading edge to reduce the risk of injury to the patient.

In one aspect, a delivery system for an implantable cardiac device is described. The system comprises an implant and a restraint. The implant has a distal end and a proximal end, and a collapsed configuration and an expanded configuration. The restraint is configured to restrain the distal end of the implant to secure the implant in its collapsed configuration for delivery to the implant site.

In some embodiments, the delivery system further comprises a delivery catheter and a tether. The delivery catheter has a proximal and a distal end and at least one channel extending therethrough. The implant is positioned proximate the distal end of the delivery catheter and restrained in the collapsed configuration by the restraint. The tether is connected to the restraint and extends through the channel of the delivery catheter to the proximal end of the delivery catheter. Manipulation of the tether causes the restraint to advance distally of the implant and release the implant from the collapsed configuration.

In some embodiments, the restraint is internally recessed to receive the distal end of the implant in its collapsed configuration. The implant may be in the form of a ring-like member having upper apices at its proximal end and lower apices at its distal end, and the restraint may be internally recessed to receive the lower apices of the ring-like member when the implant is in the collapsed configuration. The restraint may have a shaped leading edge to reduce trauma to the patient's anatomy during delivery of the implant. The delivery system may further comprise a guide catheter in which the delivery system, the implant and the restraint pass through.

In some embodiments, the restraint may further comprise a distal leading section, a central section, and a proximal cuff section. The distal section of the restraint may be shaped in a rounded manner to reduce trauma to the patient's anatomy. The proximal cuff section may be shape set so as to taper radially inwardly in a set configuration to aid in retraction through the unrestrained configuration of the implant and into the guide catheter. The restraint may be configured to surround the distal end of the implant.

In another aspect, a restraint comprises a tubular sidewall, a proximal opening, and a channel. The tubular sidewall extends from a proximal end to a distal end. The proximal opening is defined by the sidewall at the proximal end. The channel is defined by the sidewall and extends distally from the proximal opening. The restraint is configured to receive an implant in the collapsed configuration through the proximal opening to radially restrain the implant within the channel. The restraint may be used with various transcatheter delivery systems to deliver the implant.

In some embodiments, the restraint further comprises a distal end wall located at the distal end of the restraint. The proximal end of the restraint may comprise a series of proximally extending tabs defining a series of gaps between adjacent tabs. The tabs may be configured to extend proximally in a loading configuration to receive the implant and to incline radially inward in a shape set, e.g. heat set, configuration after receiving the implant.

In some embodiments, the delivery system comprises an implant comprising a tubular frame, a shaft and a collar. The tubular frame has a proximal end, a distal end and a central channel extending therethrough. The frame comprises a first pair of adjacent struts joined at a proximal apex. The shaft is carried by the proximal apex, the shaft extends along a rotation axis and has an external thread, and the shaft is configured to rotate about the rotation axis. The collar is carried by the frame and has an opening extending axially therethrough in which to receive the shaft. The collar has a complementary surface structure for engaging the threads of the shaft, and the collar is configured to at least partially surround the first pair of adjacent struts. Rotation of the shaft about the rotation axis in a first rotation direction causes the collar to advance along the first pair of struts toward the distal end of the frame to decrease an angle between the first pair of adjacent struts.

In some embodiments, the delivery system comprises the implant wherein rotation of the shaft about the rotation axis in a second rotation direction that is opposite the first rotation direction causes the collar to advance along the first pair of struts toward the distal end to allow an increase in the angle between the first pair of adjacent struts.

In some embodiments, the delivery system comprises the implant comprising an anchor coupled with the frame, the anchor configured to engage tissue of the mitral valve annulus. The frame may comprise a second pair of adjacent struts joined at a distal apex, wherein the anchor is coupled with the distal apex. The anchor may be a helical anchor.

In some embodiments, the delivery system comprises the implant comprising a tubular frame, a shaft and a collar. The tubular frame comprises a first pair of adjacent struts joined at an apex. The shaft is carried by the frame and extends along a rotation axis, the shaft having a radial engagement structure. The collar is carried by the frame and at least partially surrounding the first pair of adjacent struts, the collar having an internal complementary surface structure for engaging the radial engagement structure of the shaft. Rotation of the shaft about the rotation axis causes the collar to advance along the first pair of struts to change an angle between the first pair of adjacent struts.

In another aspect, a method of delivering an implantable cardiac device to a valve annulus includes the steps of percutaneously delivering a delivery catheter to an implant site, the delivery catheter having a proximal end and a distal end and at least one channel extending therethrough, the delivery catheter including an implant, positioned proximate the distal end of the delivery catheter, wherein a restraint, coupled to the delivery catheter by a tether, restrains the implant in a collapsed configuration. The method includes manipulating one of the implant or the tether to advance the restraint distally of the implant to release the implant from the collapsed configuration. In some embodiments, the method further includes the step of proximally retracting the restraint through the implant and delivery catheter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIG. 1A is a side view of an embodiment of a restraint after it has been advanced distally by a push wire to release an implant.

FIG. 1B is a proximal end view of the restraint of FIG. 1A.

FIG. 1C is a proximal end view of another embodiment of a restraint that may be used with the implant of FIG. 1A.

DETAILED DESCRIPTION

Figure 2A:
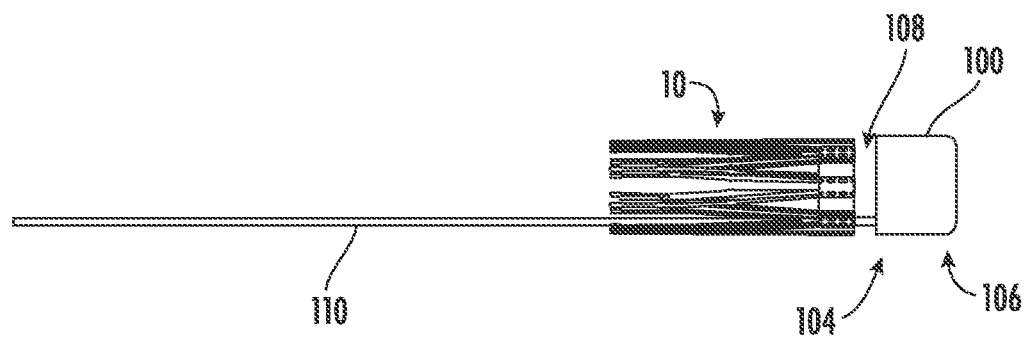
FIGS. 2A and 2B are sequential side views of the implant in its collapsed configuration being loaded into the proximal end of the restraint of FIG. 1.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

A deployment restraint is described that may be used with various implants. For example, an annuloplasty ring implant may be used to address heart valve incompetency. The implant may be delivered via transcatheter delivery. A surgeon positions the implant proximate the valve annulus, secures it in place and adjusts the implant thereby restoring the valve annulus to approximately its native configuration to restore valve leaflet function.

The implant may be delivered in either a minimally invasive (e.g. transapically) or percutaneous manner, such as transfemorally or transeptally. The implant may also be implanted surgically. Furthermore, it should be recognized that the implant can be deployed to treat mitral or tricuspid valve regurgitation.

The implant may be a mechanical prosthesis-type device capable of extending around the dilated annulus of a heart valve, engaging the tissue of the heart valve annulus, and gathering it in to a smaller diameter. More specifically, the prosthesis may be a "ring-like" design wherein the ring-like member may be formed of a shape memory material. The ring-like member may extend past the distal end of a delivery catheter. A sheath may surround the delivery catheter extending past the delivery catheter's distal end. The ring-like implant may be compressed and retained in its compressed condition by the sheath for delivery to the valve site. When the sheath is withdrawn, the ring-like implant returns to its as formed expanded diameter to engage the dilated annulus. Anchors are then advanced from the ring-like member to penetrate the tissue of the heart valve annulus. The ring-like prosthesis is then forcibly reduced in size. This reconfigures the valve annulus down to a smaller diameter, reducing and/or eliminating the regurgitation.

In practice, however, the combination of a delivery system, sheath and guide catheter presents a relatively larger profile with respect to the patient anatomy to which it must traverse. It would be preferable to reduce the profile of the overall system.

A restraint is described herein that may be used with various implants. For example, the restraint may be used with any of the implants described later below with regard to FIGS. 7-12. As further example, the restraint may be used with an implantable device that is delivered proximate and above the cardiac valve (tricuspid or mitral) annulus. The implant is subsequently implanted in the annular cardiac tissue just above the plane of the valve orifice. Details of some embodiments of the implant, such as a ring-like implantable heart valve annuloplasty ring or prosthetic, are described for example in U.S. patent application Ser. No. 15/352,288, titled "IMPLANTABLE DEVICE AND DELIVERY SYSTEM FOR RESHAPING A HEART" and filed Nov. 15, 2016, and in U.S. Provisional Patent Application No. 62/457,441, titled "IMPLANTABLE DEVICE AND DELIVERY SYSTEM FOR RESHAPING A HEART VALVE ANNULUS" and filed Feb. 10, 2017, the disclosure of each of which is incorporated by reference herein in its entirety and forms a part of this specification.

FIG. 1A is a side view of an embodiment of a restraint 100 after it has been advanced distally by a push wire 110 or other form of tether to release an implant 10. FIG. 1B is a proximal end view of the restraint 100. The implant 10, which may be a ring-like member or prosthetic, may have a series of struts 12, proximal apices or crowns 14, and distal apices or crowns 16. The implant 10 may be formed of a metal alloy, such as an alloy of nickel titanium. The distal apices 16 may have an anchor attachment interface, such as a plurality of circular openings to rotatably receive helical anchors therethrough for engaging tissue proximate the valve annulus.

The implant 10 may have upper or proximal apices 14 that form windows for receiving threaded shafts. The threaded shafts may threadingly engage with collars (for example those described in FIGS. 7-12 below), that are fitted over the apices 14. The collars may be threadingly advanced by rotation of the threaded shafts to advance the collars axially along struts 12 to change the angle of the struts as further described below.

The restraint 100 may include a sidewall 102 extending from a proximal end 104 to a distal end 106. The sidewall 102 maybe tubular. Tubular may include circular, rounded, segmented, polygonal, a closed shape, other suitable shapes, or combinations thereof. The sidewall 102 may extend longitudinally about an axis. The axis may be concentric with the sidewall 102. The sidewall 102 may comprise an extrusion of PEEK, PEBAX, Polyethylene, nylon or other known catheter shaft material, or may comprise a metal tube such as stainless steel or a titanium alloy. In some embodiments, the sidewall 102 may be a rigid, semi-rigid, soft, other type of material, or combinations thereof.

The restraint 100 may include an opening 108 at the proximal end 104. The opening 108 may be defined by the proximal end of the sidewall 102. The opening 108 may be configured to receive the implant 10 therein with the implant 10 in a collapsed, delivery configuration. The restraint 100 may include an end wall 112 at the distal end 106. The end wall 112 may close off the distal end 106 of the restraint 100. The proximal surface of the end wall 112 may act as a stop surface which the implant 10 contacts when fully inserted into the restraint 100. The distal surface of the end wall 112 may comprise an atraumatic nose cone depending upon the intended performance.

The restraint 100 may include a channel 116, as shown in FIG. 1B. The channel 116 may be an opening extending from the proximal opening 108 distally through the restraint 100. The channel 116 may extend from the opening 108 to the end wall 112.

The restraint 100 may include a leading edge 114 at the distal end 106 as shown in FIG. 1A. The edge 114 may be at the intersection of the sidewall 102 and the end wall 112. The edge 114 may be rounded in the side view as shown. In some embodiments, the edge 114 may be circular, beveled, other rounded shapes, other suitable shapes, or combinations thereof. The edge 114 may provide an atraumatic distal end 106 of the restraint 100. The restraint 100 may have a "bull-nosed" distal end 106. The atraumatic distal end 106 may reduce the risk of injury upon distal release of the restraint 100. The atraumatic tip may aid in advancing the delivery system through patient anatomy to minimize injury to cardiac structures such as the left atrium.

The push wire 110 may be integral with the restraint 100 and may be manually manipulated to advance (or retract) the restraint 100. The wire 110 may have a compressive stiffness (column strength) sufficient to apply distal forces to the implant 10 to distally advance the restraint 100 from the distal end of the implant 10. Wire 110 may be cannulated (e.g. a hypotube) if desired to allow infusion of drugs.

FIG. 1C is a proximal end view of an embodiment of a restraint 100A having a plurality of internal recesses 118. As shown, the restraint 100A may have internal recesses 118 for receiving the distal apices 16 of the implant (FIG. 1A). The recesses 118 may be along an inner surface 103 or surfaces of the sidewall 102. There may be a plurality of the recesses 118 circumferentially spaced apart along the sidewall 102 and extending in an axial direction. There may be at least two, four, six, eight, ten, twelve, fourteen, sixteen, eighteen or more recesses 118. Radially inwardly projecting ridges of the inner surface 103 may extend between adjacent recesses 118. The ridges of the inner surface 103 may be sized appropriately to allow for the implant 10 to be securely inserted into the restraint 100.

The sidewall 102 may provide radially inward counter forces as a reaction to radially outward forces from the collapsed implant 10. The sidewall 102 may therefore provide radial resistance or stiffness sufficient to secure the implant 10 in the collapsed configuration. The sidewall 102 may have a fixed shape. In some embodiments, the sidewall 102 may be flexible or conformable.

In some embodiments, the sidewall 102 may comprise an annular strip or loop of material configured to secure a distal end of the implant 10, with or without an end wall 112. For example, the restraint 100 may be an axially shortened sidewall 102 having an axial length of no more than about 1 cm, no more than about 5 mm or 3 mm or less, surrounding only a short axial portion of the distal end of the implant 10. The implant 10 may have sufficiently stiff struts 12 such that restraining only a portion of the distal end of the implant 10 maintains the implant 10 in the collapsed configuration. The loop may be attached to the push wire 110 by solder, crimping, or threadable engagement with the end wall 112 or with the sidewall 102. The push wire 110 may be advanced distally to advance the loop distally and release the implant 10.

Figure 2B:
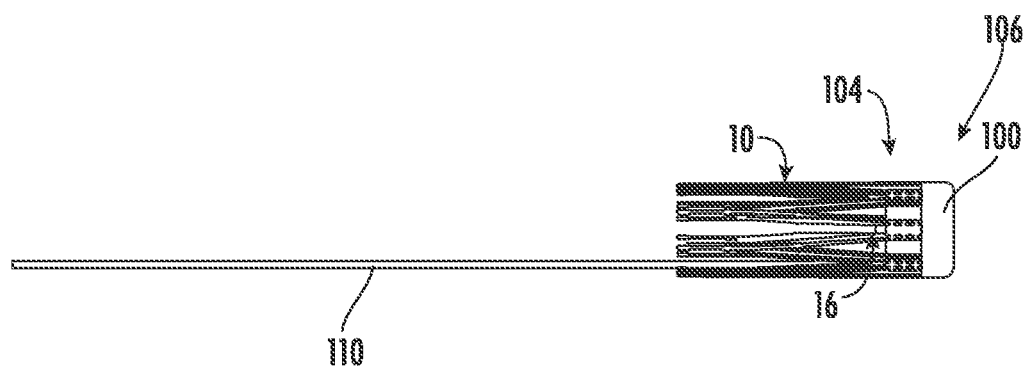

FIGS. 2A and 2B are sequential side views of the implant 10 in its collapsed configuration being loaded into the proximal end 104 of the restraint 100. The implant 10 is compressed in a collapsed delivery configuration. In FIG. 2B, the distal end or apices 16 of the implant 10 are received through the opening 108 and into the channel 116 within the restraint 100. The restraint 100 will secure the implant 10 in a substantially collapsed state, as shown in FIG. 2B. The push wire 110 may be manipulated and advanced axially distally, moving the restraint 100 axially and distally away from the implant 10 thereby removing the constraining force on the implant 10 allowing it to return to its expanded shape, similar to that shown in FIG. 1A.

In some embodiments, the implant 10 may be secured from advancing distally when the restraint 100 is advanced distally. For example, the implant 10 may be secured by the delivery catheter or a releasable tether. In some embodiments, the restraint 100 is configured to slide off the secured implant 10 with a particular distally applied force to overcome proximal direction friction forces acting on the inner surface 103 of the restraint 100 from the radially outward forces of the implant 10. In some embodiments, the restraint 100 may be released from the implant 10 by retracting the implant 10 proximally while either advancing the restraint 100 distally or maintaining the axial position of the restraint 100.

After the implant 10 is released from the restraint 100, the restraint 100 may remain in a position distally relative to the implant 10, as shown in FIG. 1A. In some embodiments, the restraint 100 may be advanced farther distally, for example into the ventricle. In some embodiments, the restraint 100 may be retracted proximally so as not to interfere with the implantation of implant 10. The restraint 100 may be retracted proximally through the expanded implant 10. The restraint 100 may be retrieved by proximal advance of the push wire 110 back into the delivery catheter.

Figure 3:
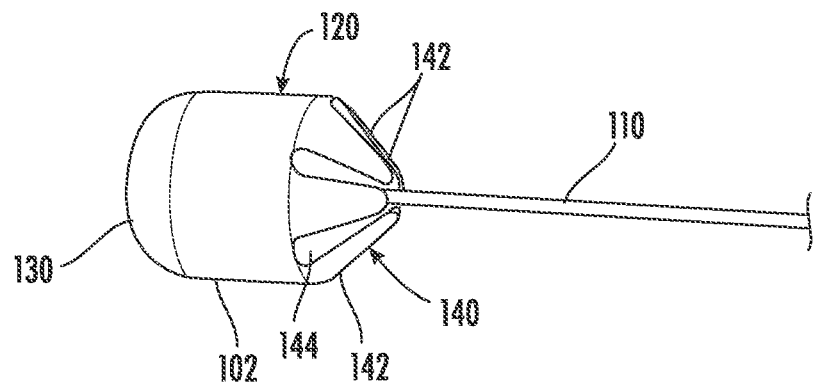
FIG. 3 is a perspective view of another embodiment of a restraint having proximally extending tabs and shown in a shape set configuration.

FIG. 3 is a perspective view of another embodiment of a restraint 120. The restraint 120 may have the same or similar features and/or functionalities as the restraints 100, 100A, and vice versa. The restraint 120 may be made from a shape memory nickel titanium alloy. FIG. 3 shows the restraint 120 in a heat set or shape set configuration. The restraint 120 may have proximally extending tabs 142, shown in a shape set configuration in FIG. 3, the tabs extending proximally from a proximal end of sidewall 102. The restraint 120 comprises a distal end 130 and a proximal end 140. The distal end 130 may have an atraumatic rounded distal section, or leading edge. The proximal end 140 may have a proximal slotted and tapered cuff section. The proximal end 140 may include a series of tabs 142 extending proximally and biased radially inwardly to produce a conical proximal face. The tabs 142 may be separated by gaps 144 between adjacent tabs 142. There may be at least two, four, six, eight, ten, twelve or more tabs 142 and corresponding number of gaps 144.

Figure 4:
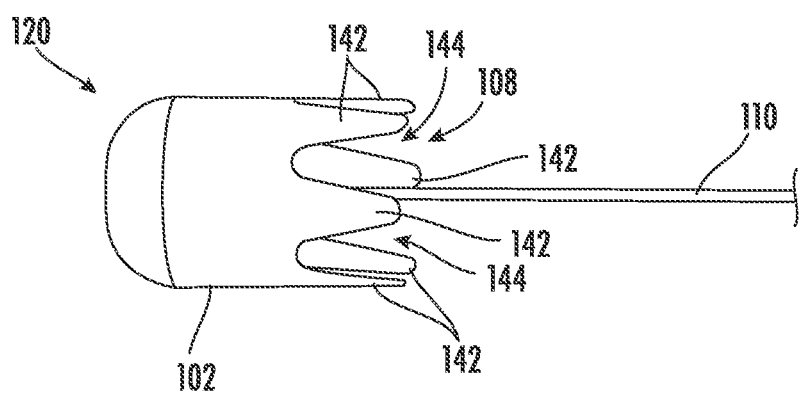
FIG. 4 is a side view of the restraint of FIG. 3 with the proximally extending tabs radially expanded to receive an implant in a collapsed configuration.

FIG. 4 is a side view of the restraint 120 with the proximally extending tabs 142 radially expanded. The tabs 142 may be expanded to receive the implant 10 in a collapsed configuration through the proximal opening 108. The restraint 120 may receive the distal end or distal apices 16 of the implant 10 (FIG. 1A). After the restraint 120 is displaced distally from the implant 10, the proximal end 140 may return to its conical shape set configuration of FIG. 3. This configuration may aid in the retraction of the restraint 120 through the implant 10 and into the delivery guide catheter, for example by reducing the risk of snagging the restraint 120 on the implant 10, facilitating guiding the restraint 120 back into the delivery catheter, etc.

The restraints 100, 100A, 120 provide many advantages. For example, the restraints reduce the overall profile (e.g.

diameter) of the delivery system, more specifically the guide catheter, as more clearly shown in and described with respect to FIGS. 5 and 6.

Figure 5A:
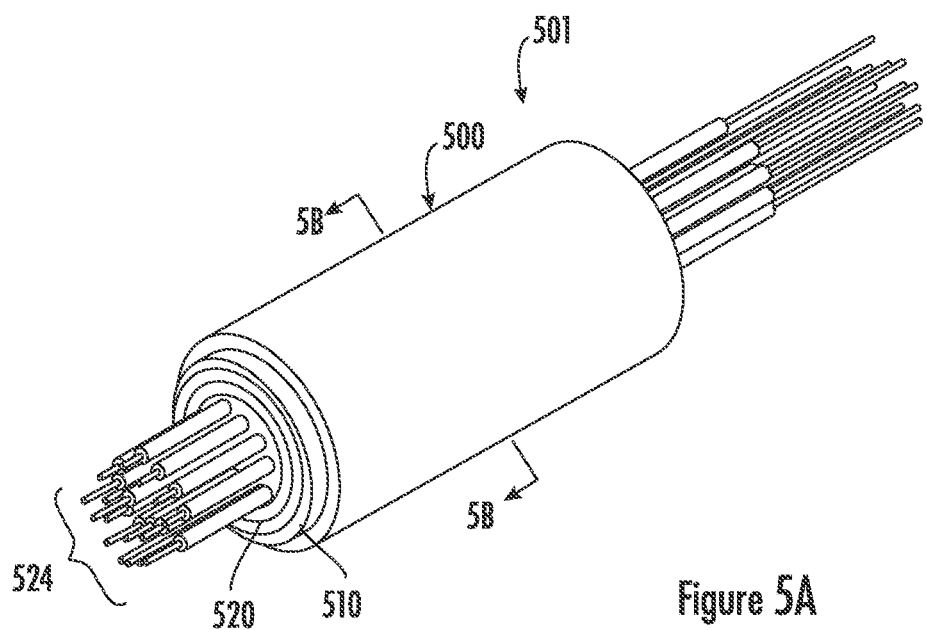
FIG. 5A is a partial perspective view of an embodiment of a delivery system for delivery of a cardiac implant, the system having a sheath to restrain the implant during delivery to the heart.
Figure 5B:
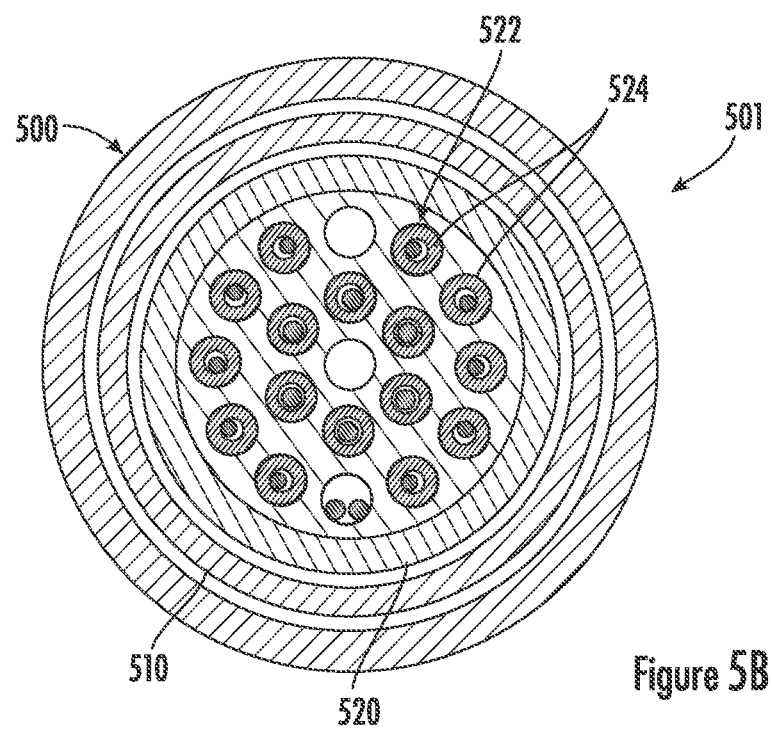
FIG. 5B is a cross section view of the system of FIG. 5A as taken along the line 5B-5B as indicated in FIG. 5A.

FIG. 5A is a partial perspective view of an embodiment of a delivery system 501 for delivery of a cardiac implant. FIG. 5B is a cross section view, taken along section 5B-5B of FIG. 5A, of the system 501. The system 501 includes a sheath 510 to restrain the implant 10 during delivery to the heart. The system 501 includes a delivery catheter 520 having a series of channels 522 containing the drivers 524 for actuating the anchors and/or the collars of the implant, as described further below with regard to FIGS. 7-9. The sheath 510 extends distally beyond the delivery catheter 520 and drivers 524, surrounding the delivery catheter 520 and the implant 10 which is coupled to the drivers 524 and extends distally past the delivery catheter 520. The sheath 510 is used to constrain the implant 10 during delivery to the implant site proximate the heart valve annulus. Due to the presence of the sheath 510, a guide catheter 500 with a sufficiently large width may be used to accommodate the delivery catheter 520 and the sheath 510. In some embodiments, the guide catheter 500 is a 33 French delivery catheter.

Figure 6A:
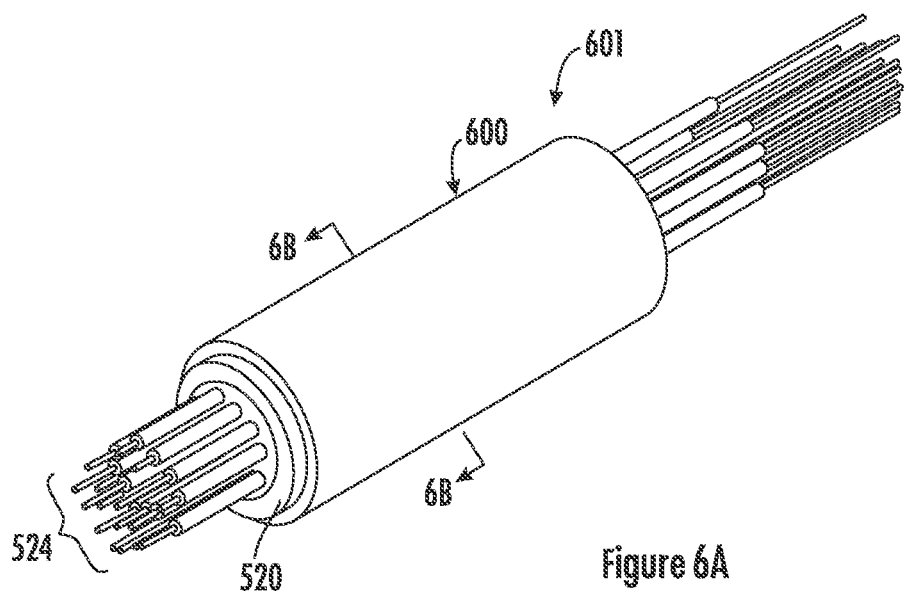
FIG. 6A is a partial perspective view of an embodiment of a delivery system for delivery of a cardiac implant, the system having an embodiment of a restraint and a reduced-size guide catheter.
Figure 6B:
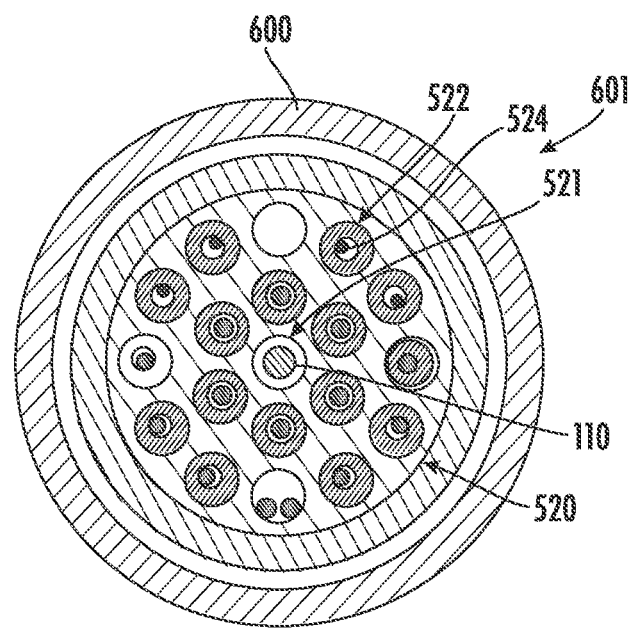
FIG. 6B is a cross section view of the system of FIG. 6A, taken along the line 6B-6B as indicated in FIG. 6A.

FIG. 6A is a partial perspective view of an embodiment of a delivery system 601 for delivery of a cardiac implant. FIG. 6B is a cross section view, taken along section 6B-6B of FIG. 6A, of the system 601. The system 601 employs the deployable restraint described herein and a reduced-size guide catheter compared to the system 501 of FIGS. 5A and 5B. As shown in FIGS. 6A and 6B, the delivery system 601 includes the push wire 110, which may be attached to the restraint 100, and used in lieu of the sheath 510 to constrain the implant. Here, the push wire 110 is extending through a central channel 521 of the delivery catheter 520. The restraint 100 restrains the implant 10 (FIG. 1A), rendering the sheath 510 unnecessary. As such, a smaller width catheter 600, such as a 28 French guide catheter, can now be used to advance the delivery catheter 520, the push wire 110 and the restraint 100 from outside the patient toward and into an atrium of the patient. The restraint may, therefore, significantly reduce the overall diameter of the guide catheter, for example by greater than 15% or more. Any of the restraints described herein may be used with the system 601, such as the restraints 100, 100A or 120, etc.

The discrete nature of the deployable restraint 100, 100A or 120 also allows for easier navigation of bends and turns within the channel of the guide catheter and the patient's anatomy, including the atrium. It is also within the scope of the invention that one or more tethers (push wires, etc.) may be incorporated into the system for moving the restraint 100, 100A or 120. The tethers may be contained in one or more channels of the delivery catheter, for example as described above.

Figure 7:
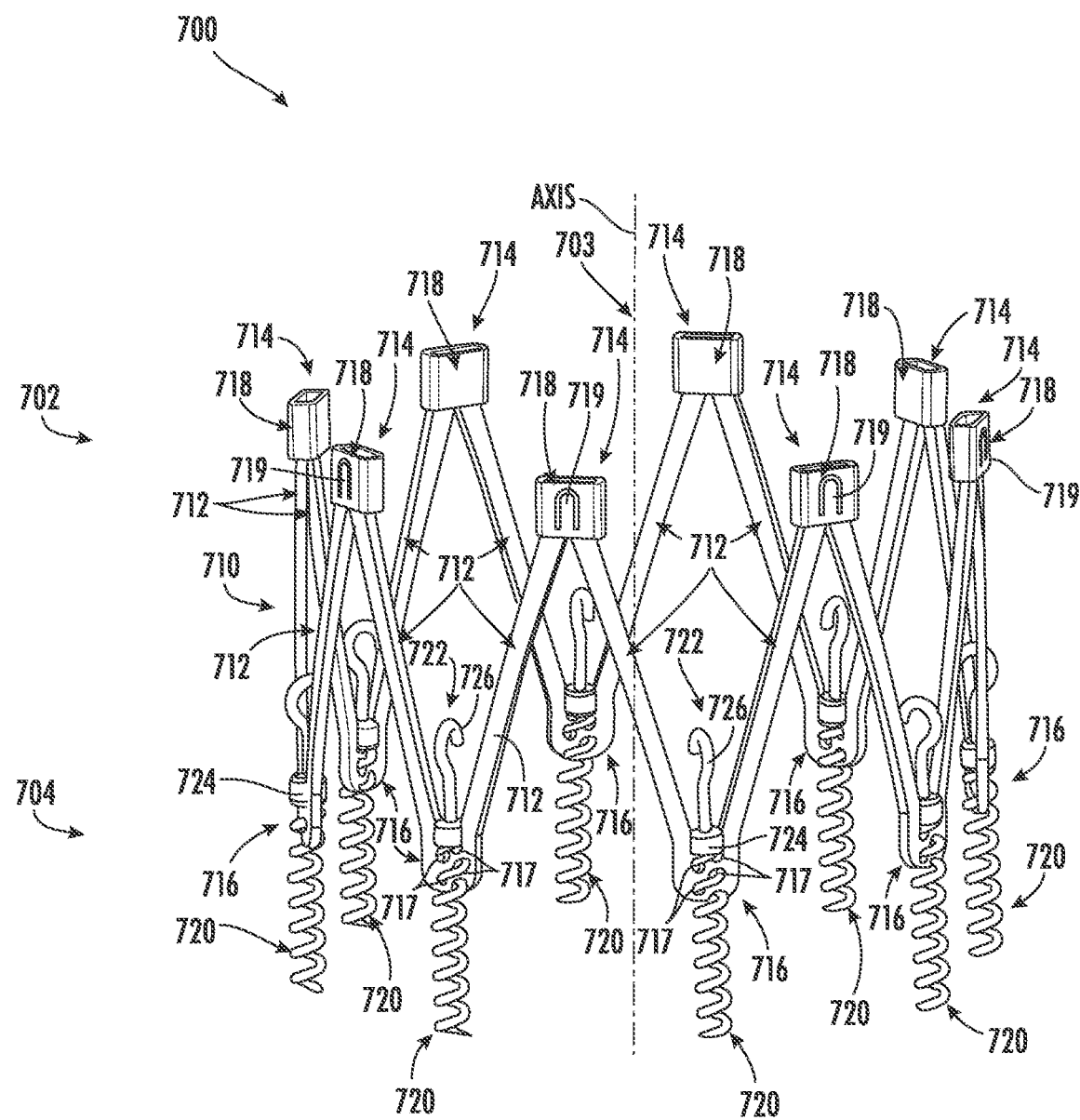
FIG. 7 is a perspective view of an embodiment of an exemplary implant that may use the restraint disclosed above, having a frame, collars and anchors, for reshaping a heart valve annulus.
Figure 8:
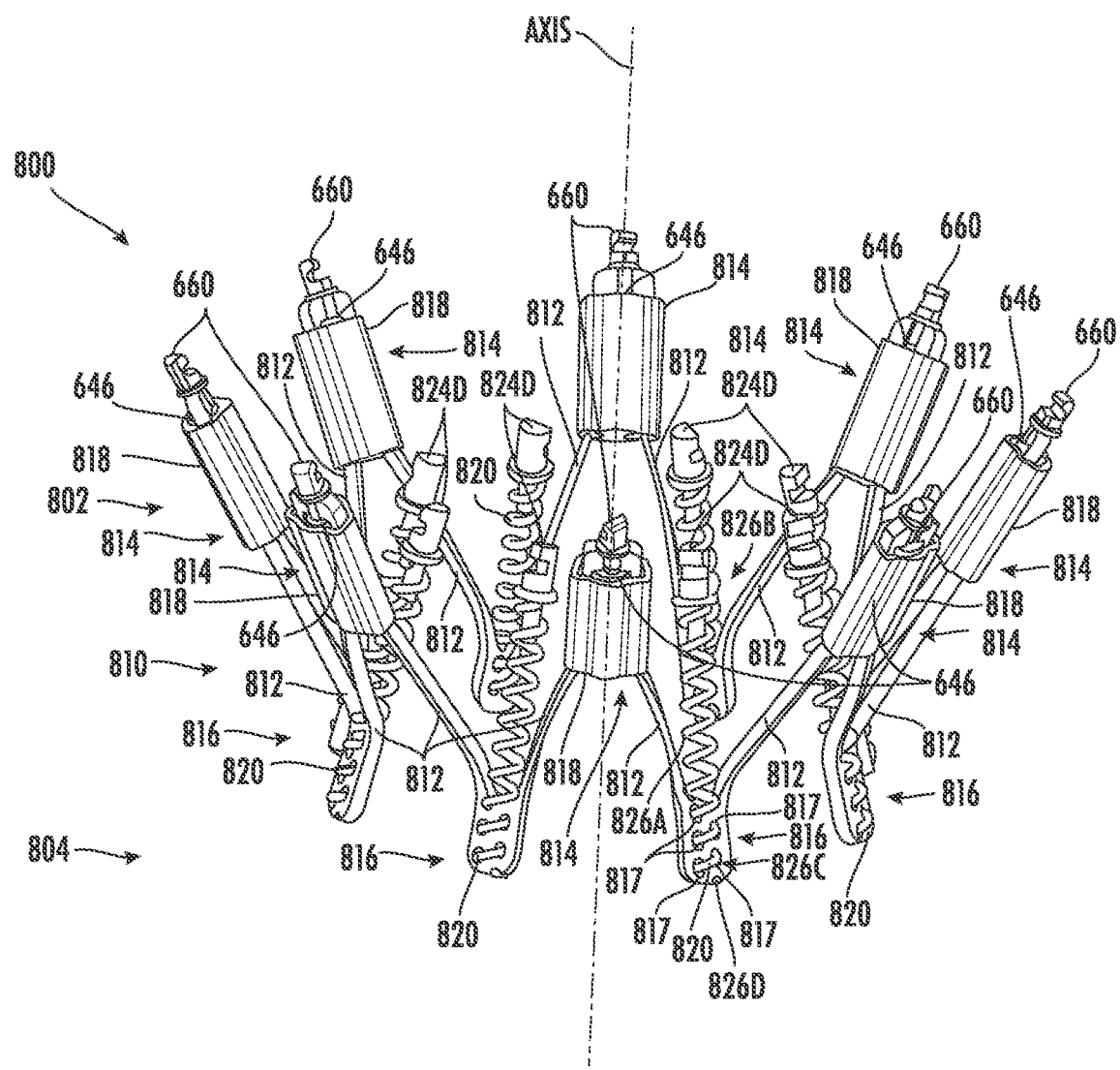
FIG. 8 is a perspective view of an embodiment of an implant having a rotatable threaded shaft for use with an axially translatable collar according to aspects disclosed herein.
Figure 9:
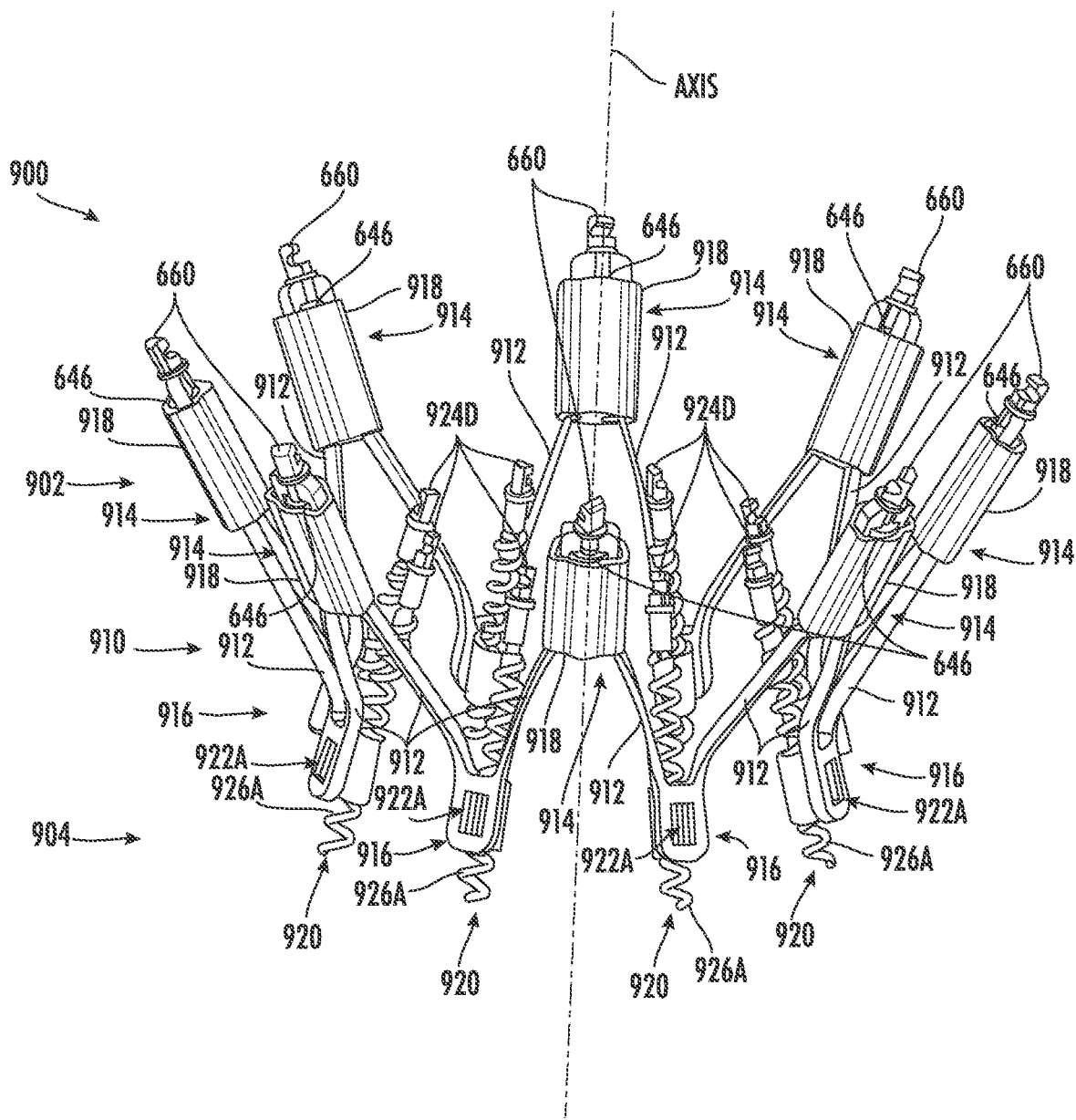
FIG. 9 is a perspective view of an embodiment of an implant having a rotatable threaded shaft for use with an axially translatable collar and anchor and housing assemblies at a distal end of a frame according to aspects disclosed herein.

FIGS. 7-9 illustrate various implants which may include a restraint as described in various embodiments herein to secure the implant during deployment. FIG. 7 is a perspective view of an embodiment of an implant 700 that may use the restraint disclosed above, having a frame, collars and anchors, for reshaping a heart valve annulus. With reference to FIG. 7, the implant 700 is an implantable device. The implant 700 forms a lumen or opening 703 extending through the implant 700. For sake of description, a geometric reference longitudinal axis is indicated. The implant 700 may be described with reference to the axis. An "axial" direction refers to movement generally parallel to the axis in either an upward or downward direction, unless otherwise indicated. The opening 703 extends axially between an upper portion 702 of the implant 700 and a lower portion 704 of the implant 700. The upper and lower portions 702, 704 may include various features of the implant 700. The terms "upper," "upward," and the like refer to directions generally toward the upper portion or proximal end 702, and the terms "lower," "downward," and the like refer to directions generally toward the lower portion or distal end 704, unless otherwise indicated. "Proximal" refers to a direction in the upward direction, and "distal" refers to a direction in the downward direction. The terms "inner," "inward," and the like refer to directions generally toward the axis, and terms "outer," "outward," and the like refer to directions generally away from the axis. These geometric references generally apply unless otherwise indicated, either explicitly or by context.

The implant 700 includes a frame 710. The frame 710 extends circumferentially around and partially axially along the axis. The axis may be defined by the frame 710. The frame 710 is generally symmetric with respect to the axis. However, the frame 710 need not be symmetric with respect to the axis. The frame 710 has a generally tubular shape. "Tubular" includes circular as well as other rounded or otherwise closed shapes. The frame 710 is generally circular about the axis. The frame 710 may be circular, rounded, ellipsoidal, segmented, other shapes, or combinations thereof. The frame 710 may change shape, size, configuration, etc. The frame 710 may have various shapes, sizes, configurations etc. at various phases of use, e.g. pre-delivery, during delivery, after engagement with tissue, after contracting the annulus, post-contraction, during the lifetime of use while implanted, etc.

The implant 700 includes one or more struts 712. The struts 712 may form all or part of the frame 710. The struts 712 are elongated structural members. The struts 712 and/or other parts of the frame 710 are formed of a metal alloy. The struts 712 and/or other parts of the frame 710 may be formed of an alloy of nickel titanium. In some embodiments, the struts 712 and/or other parts of the frame 710 are formed of other metals, metal alloys, plastics, polymers, composites, other suitable materials, or combinations thereof. There are sixteen struts 712. In some embodiments, there may be fewer or more than sixteen struts 712. In some embodiments, there may be at least two, four, six, eight, ten, twelve, fourteen, eighteen, twenty, twenty-two, twenty-four, twenty-six, twenty-eight, thirty, or more struts 712.

The struts 712 may be part of the same, monolithic piece of material (e.g. tube stock). Thus, the struts 712 may refer to different portions of the same, extensive component. The struts 712 may be formed from the same piece of material. The struts 712 may be formed separately and attached permanently together, e.g. by welding, etc. In some embodiments, the struts 712 may be separate components that are detachably coupled together by other components of the implant 700. For example, the struts 712 may be held together via various components described herein, such as collars 718, anchors 720, other features, or combinations thereof. In some embodiments, separate strut units may include two or more struts permanently attached together such as at an apex, and the separate units may each be coupled together, either permanently or detachably, to form the frame 710. In some embodiments, the struts 712 may be attached by hinges, pins, or other suitable means.

The elongated, middle portions of the struts 712 have a generally rectangular cross-section but can vary in circumferential width and radial thickness to allow for different beam characteristics and forces applied as the collars are advanced. This may facilitate for example post implantation constriction or remodeling of the annulus, as further described. The long ends of the rectangular cross-section of the struts 712 extend along the circumference of the frame 710. "Circumference" as used herein generally refers to a perimeter or boundary and can refer to a circular or other rounded or non-rounded path lying in a plane substantially transverse to the axis, unless otherwise stated. The short ends of the rectangular cross-section of the struts 712 extend transversely to the circumference of the frame 710. In some embodiments, other configurations and/or cross-sectional shapes of the struts 712 may be implemented. The cross-section may be rounded, circular, other shapes, or combinations thereof.

The struts 712 extend around the axis to form the various shapes of the frame 710. The struts 712 are arranged such that the wall pattern of the frame 710 may be approximately sinusoidally or zig-zag shaped. In some embodiments, the wall pattern may have other suitable shapes, sinusoidal or otherwise. The vertices of the sinusoidal shaped frame 710 may be pointed or rounded.

Pairs of adjacent struts 712 meet at an apex. At least a first pair of adjacent struts 712 meets at an upper apex or crown 714 at the upper portion 702 of the implant 700. At least a second pair of adjacent struts 712 meets at a lower apex or crown 716 at the lower portion 704 of the implant 700. The terms "apex," apices," and the like may be used interchangeably with terms "crown," "crowns," and the like, as used herein and as used in any reference incorporated by reference herein, unless otherwise stated. The upper and lower crowns 714, 716 are spaced sequentially along the circumference of the frame 710, with one of the upper crowns 714 followed by one of the lower crowns 716, followed by another one of the upper crowns 714, etc. In the illustrated embodiment, there are eight upper crowns 714 and eight lower crowns 716. In some embodiments, there may be no more than about six or four or fewer or more than eight or ten or twelve upper and lower crowns 714, 716, depending on the number of struts 12 and the resulting number of apices.

The upper crowns 714 are each configured to have a restraint such as a collar 718 fitted over and/or around the upper crown 714. Thus, the upper crowns 714 may include various features, dimensions, etc. as described herein for coupling with the collar 718, as further described. The upper crowns 714 are shown partially covered by the collars 718 in FIG. 7. The upper ends of the upper crowns 714 may move distally toward the lower portion 704 of the implant 700 relative to their position in FIG. 7 to expose the upper crowns. In some embodiments, one or more of the upper crowns 714 may not have the collar 718. In some embodiments, fewer than all of the upper crowns 714 are configured to receive the collar 718. In some embodiments, all of the upper crowns 714 may be configured to receive the collar 718 but when implanted only some of the upper crowns 714 may actually include the collar 718.

At least two and optimally at least four or six or all of the lower crowns 716 are configured for coupling with an anchor 720. The anchor 720 is moveably coupled with the lower crown 716. The anchor 720 engages with tissue of the heart, for example the annulus, to secure the implant 700 to the tissue, as described above. Movement of the anchor 720 relative to the lower crowns 716 causes the anchor 720 to penetrate the tissue. The lower crowns 716 may include a variety of engagement features to allow such movement of the anchors 720, such as flanges and/or the openings 717. The lower crowns 716 each include a series of the openings 717 extending through the lower crowns 716. The openings 717 extend in two spaced columns in the axial direction along the lower crown 716. The openings 717 in each column are alternately located in the axial direction, as shown, to accommodate receipt of the anchor 720 therein. Other configurations and/or spacings of the openings 717 may be implemented. For clarity, only some of the openings 717 are labeled in FIG. 7. The openings 717 are shown as circular holes. Other shaped openings 717 may be implemented.

The openings 717 of the lower crown 716 are configured to rotatably receive a helical segment of the corresponding anchor 720 such that the anchor extends sequentially through the openings 717, both while the anchor 720 moves relative to the struts 712 and while the anchor 720 is stationary relative to the struts 712, as further described herein. In some embodiments, features alternative to or in addition to the openings 717 may be used to couple the anchor 720 with the corresponding lower crown 716. In some embodiments, fewer than all of the lower crowns 716 may be configured for coupling with the anchor 720. Thus, one or more of the lower crowns 716 may not have the openings 717 and/or other features for coupling with the anchor 720. In some embodiments, all of the lower crowns 16 may be configured for coupling with the anchor 720, but when implanted only some of the lower crowns 716 may actually include the anchor 720.

The struts 712 are reconfigurable about the upper and lower crowns 714, 716. Pairs of adjacent struts 712 that meet at the upper and lower crowns 714, 716 can move angularly relative to each other. Such movement may be described as a rotation or pivot of the adjacent struts 712 about the corresponding upper or lower crown 714, 716. For example, two adjacent struts 712 forming the upper crown 714 may be moved such that the struts 712 effectively rotate relative to each other about the upper crown 714. For example, two adjacent struts 712 forming the lower crown 716 may be moved such that the struts 712 effectively rotate relative to each other about the lower crown 716. "Rotation" of the struts 712 as described includes pinching together of the struts 712, for example by distal advancement of the collar 718. Thus, adjacent struts 712 may not include an actual rotatable hinge, pin, or other rotation features. Movement of the struts 712 closer together to decrease the angle therebetween is described as a "closing" of the struts 712. Movement of the struts 712 farther apart to increase the angle therebetween is described as an "opening" of the struts 712.

The struts 712 may be biased to an enlarged cross-sectional configuration in the absence of an external force applied to the struts 712. Application of an external circumferentially compressive force to the struts 712, for example with the collar 718, causes the struts 712 to move angularly, for example to close. Movement of the struts 712 in this closing manner also causes the implant 700 to decrease its circumference (e.g. diameter) in the case of a circular implant 700. In its free, unconstrained state, the frame 710 may be in an enlarged configuration. Application of the compressive circumferential force causes the circumference of the frame 710 to reduce. Removal or lessening of the circumferential force allows the frame 710 to open. The circumferential force may be increased or decreased by moving the collar 718 farther downward or upward, respectively, in the axial direction, as further described herein. The collar 718 may lock in place after translating axially down the upper crown 714 to secure the implant 700 at a particular width.

The implant 700 includes one or more restraints such as the sliders or collars 718. The terms "collar," collars," and the like may be used interchangeably with the terms "slider," "sliders," "sliding members," and the like, as used herein and as used in any reference incorporated by reference herein, unless otherwise stated. As shown in FIG. 7, the implant 700 includes eight collars 718. In some embodiments, there may be fewer or more than eight collars 718. The number of collars 718 may correspond to the number of upper crowns 714. In some embodiments, there may be fewer collars 718 than upper crowns 714. Thus, in some embodiments, some upper crowns 714 of the frame 710 may not include the collar 718. The collars 718 may translate axially due to axial applied force. The collars 718 may translate axially due to engagement with a central rotating shaft as described below with regard to FIG. 8.

The collar 718 couples with the corresponding upper crown 714. The collar 718 may be fitted over the upper crown 714. The collar 718 forms an inner opening at least partially therethrough and into which the upper crown 714 is received as the collar 718 fits over the upper crown 714. The collar 718 may have a rectangular profile as shown. In some embodiments, the collar 718 may have other profiles, e.g. rounded, segmented, polygonal, other suitable shapes, or combinations thereof. The profile of the collar 718 may be a closed shape, as shown, or it may be an open shape such as a "C" shape. The collar 718 thus at least partially surrounds the corresponding upper crown 714. As shown, the collar 718 completely surrounds the corresponding upper crown 714. In some embodiments the collar 718 may not completely surround the upper crown 714. The collar 718 engages with the upper crown 714.

The collar 718 may engage with circumferentially opposed sides of the upper crown 714 and/or adjacent struts 712. The collar 718 engages with and may be advanced downward over the upper crown 714 to angularly move the corresponding pair of adjacent struts 712 towards each other. The collar 718 may apply a compressive circumferential force to the struts 712 to cause the struts 712 to decrease the angle between the struts 712. The circumferential force may be applied inwardly to the struts 712 and towards the upper crown 714. Thus, a vertical force applied to the collars 718 may be translated into a circumferential force on the struts 712. By "circumferential" it is meant that the direction of the forces is along the outer perimeter or boundary of the frame 710 as viewed from the top or bottom of the frame 710 and is not meant to limit the shape of the frame 710 to a circle. Movement of the collar 718 over the struts 712 moves, e.g. rotates, the struts 712 such that the angle between the adjacent struts 712 decreases. A first circumferential force may be applied to one of the struts 712 by the collar 718 and a second circumferential force that is opposite in direction to the first circumferential force may be applied to the adjacent strut 712 by that same collar 718. The farther the collar 718 is moved down over the struts 712, the more the struts 712 move and the more the angle decreases, causing the frame 710 to decrease in width, e.g. diameter. The struts 712 thus move relative to each other about the upper crown 714 due to movement of the collar 718. The collar 718 may lock in place, for example with a locking tab 719. The collar 718 may include the locking tab 719. The locking tab 719 provides an engagement feature for the collar 718 to engage with the struts 712. The locking tab 719 locks the collar 718 in place on the upper crown 714 after movement of the collar 718 over the upper crown 714. The locking tab 719 is biased toward the inner opening formed by the collar 718. The locking tab 719 may be shape set to take on an inwardly oriented bias. The collar 718 and/or features thereof such as the locking tab 719 are formed of a nickel titanium alloy such as Nitinol. In some embodiments, the collar 718 and/or features thereof such as the locking tab 719 are formed of other materials, such as metals, other metal alloys, plastics, polymers, composites, other suitable materials, or combinations thereof. Further details of various embodiments of the collar 718, and features thereof such as the locking tab 719, are described herein.

The collars 718 may thus provide one or more functions for the implant 700. In some embodiments, the collars 718 may cinch the frame 710, as described. In some embodiments, the frame 710 may be cinched by features in addition to or alternatively to the collars 718, and the collars 718 may restrain the frame 710 in the cinched state. In some embodiments, the collars 718 may thus not cinch the frame 710 but only restrain the frame 710 in the cinched state. In some embodiments, the collars 718 may cinch the frame 710 as well as restrain the frame 710 in the cinched state.

The implant 700 includes one or more anchors 720. In some embodiments, the anchors 720 may be part of anchor assemblies, may include distal helical portions and proximal anchor heads, and/or may include a proximal coupling as described in FIG. 8. The anchors 720 of FIG. 7 have anchor heads 722 attached at their upper or proximal ends. Each anchor head 722 may comprise an abutment 724 and an engagement structure such as a hook 726. The abutment 724 may be a cap portion on an upper end of the anchor 720. The abutment may be cylindrical. The abutment 724 may have a width sized to limit axial advance of the anchor 720, as described herein. The hooks 726 are elongated, over-hanging members. The hooks 726 may provide an engagement for a delivery tool. The hooks 726 may interact with a delivery tool to rotate and axially advance the anchors 720. In some embodiments, features other than the hooks 726 may be used, for example eye bolts.

The anchors 720 are made of a suitable biocompatible metal alloy such as stainless steel, cobalt chromium, platinum iridium, nickel titanium, other suitable materials, or combinations thereof. Each anchor 720 is sharpened at its distal point, or leading turn, so as to facilitate penetration into the cardiac tissue. Each anchor 720 may be from about ten to about fifteen millimeters (mm) in total axial length. In some embodiments, the anchors 720 may be shorter or longer than ten to fifteen millimeters (mm) in total axial length. By "total" axial length it is meant the axial length of the anchor 720 from the end of the distal penetrating tip to the opposite, proximal end of the head 722. The helical portion of the anchor 720 may be from about six to about twelve millimeters (mm) in axial length, i.e. in an axial direction. In some embodiments, the helical portion of the anchor 720 may be shorter or longer than six to twelve millimeters (mm) in axial length. The anchor head 722 and/or other non-helical portions of the anchor 720 may be from about three to about four millimeters (mm) in axial length. In some embodiments, the anchor head 722 and/or other non-helical portions may be shorter or longer than three to four millimeters (mm) in axial length. The anchors 720 are capable of extending from about four to about seven millimeters (mm) axially beyond the corresponding lower crown 716. For example, the helical portions of the anchors 720 may extend from four to seven millimeters (mm) into the cardiac tissue. As mentioned, the frame 710 is shown with eight upper crowns 714 and eight lower crowns 716 and anchors 720, but this number of apices is shown for illustration purposes and may be varied, for example four upper and lower apices, sixteen upper and lower apices, etc. In some embodiments, regardless of the number of apices, each upper crown 714 is fitted with a collar 718 and each lower crown 716 has a respective anchor 720 threadingly received through the openings 717 of the anchor 720.

The anchors 270 couple with the lower crowns 716. The anchors 720 may be in the general shape of a helix. As shown, the openings 717 receive helically wound anchors 720. The openings 717 are spaced to accommodate the pitch of the helical anchors 720, for example the spacing between the turns in the helix of the anchor 720. There may be a gap between the inner diameter of the openings 717 and the outer diameter of the anchor 720 to allow for free movement of the anchor 720 through the openings 717. There may be a small gap between the inner diameter of the openings 717 and the outer diameter of the anchor 720. In some embodiments, there may be an interference fit between the openings 717 and the anchor 720 or a varying pitch to provide interference between the anchor and frame. In some embodiments, the anchors 720 may instead engage anchor housings at the lower crowns 716, as described in FIG. 9 below.

FIG. 8 is a perspective view of an embodiment of an implant 800 having a proximal end 802 and a distal end 804 with a central lumen extending therethrough along the axis as indicated. The implant 800 may be configured for catheter-based delivery. In treating the mitral valve, for example, a delivery catheter is inserted via a puncture in the femoral vein, after which it traverses the inferior vena cava, into the right atrium and passes through the septum separating the right and left atria. It is then directed distally towards the mitral annulus, aligning the distal end of the catheter and the implant 800 with the mitral annulus.

The implant 800 is shown having the frame 810 with rotatable shafts 646 and axially translatable collars 818 at the proximal apexes 814. The proximal end of the rotatable shafts 646 each include a coupling 660 for engagement and rotation by a driver or adjustment catheter to rotate the shaft 646. As further describe herein, rotation of the shaft 646 causes the collar 818 to advance along the struts 812 to change, e.g. increase or decrease, the angle between the struts 812 to radially contract or expand the implant 800. Each distal apex 816 includes the helical anchor 820 engaged with openings 817 of the corresponding distal apex 816. Each anchor 820 includes a helical portion 826A, proximal portion 826B and a distal portion 826C. The distal portion 826C may end at a tip 826D. The tip 826D may be a sharpened point configured to pierce the cardiac tissue. On the proximal end of the proximal portion 826B is a coupling 824D. The coupling 824D may be engaged and rotated by a driver or adjustment catheter to rotate the anchor 820 through the openings 817 and into tissue. Each coupling 660 and 824D may be engaged and rotated by its own driver or adjustment catheter. Thus, there may be such a driver for each coupling 660, 824D. The collars 818 and anchors 820 are shown in a relative proximal position and may be adjusted proximally or distally therefrom to effect various changes in the frame 810. The implant 800 of FIG. 8 may have any of the same or similar features and/or functionalities as any other implant described herein, including but not limited to the implant 700 of FIG. 7, the implant 900 of FIG. 9, and vice versa.

Eight collars 818 and eight shafts 864 are shown in FIG. 8. There may be fewer or more collars 818 and shafts 646, for example one collar 818 and one shaft 646 located at at least two or three or four or at each proximal apex of the frame 810. The threaded shaft 646 is located, for example nested, secured, retained, etc., within a portion of the frame 810 and located internally to the collar 818. In some embodiments for driving the collar 818 over an apex formed by a pair of adjacent struts 812, the threaded shaft 646 may be rotated internally to the collar 818. Rotational motion of the threaded shaft 646 is transmitted from external engagement features, such as threads, of the threaded shaft 646 to corresponding internal features, such as internal threads or teeth, of the collar 818, to result in axial movement of the collar 818. As the collar 818 moves distally, it causes adjacent struts 812 to move closer together, decreasing the angle between the struts 812, and causing the implant 800, for example the frame 810, to reduce in width, e.g. diameter. The collar 818 may remain or substantially remain rotationally stationary relative to the struts 812. Thus, for example, the threaded shaft 646 may be rotated while remaining axially stationary and the collar 818 may translate axially while remaining rotationally stationary or substantially rotationally stationery. By "substantially rotationally stationery" it is meant that the collar 818 may rotate some amount after which further rotational movement is prevented, for example due to play between the collar 818 and the struts.

Various modifications of the implant 800 may be implemented. For example, in some embodiments, the threaded shaft 646 may axially translate. In some embodiments, the collar 818 may rotate. In some embodiments, the collar 818 may be rotated and move axially, while the threaded shaft 646 remains rotationally and axially stationary. The mechanical communication between outer threads of the threaded shaft 646 and the inner features (such as threads) of the collar 818 may be direct communication, such as contact between the respective threads and features. In some embodiments, the mechanical communication may be indirect, for example with intervening structures such as bushings and the like, coatings, etc. in between the respective engagement features. These and other modifications to the implant 800 that are still within the scope of the disclosure will be apparent in light of the further details and description herein.

FIG. 9 is a perspective view of the implant 900 including a frame 910 formed of struts 912 and having a proximal end 902 and distal end 904. The proximal end 902 of the implant 900 includes the shafts 646 with proximal couplings 660 and collars 918 surrounding pairs of adjacent struts 912 at proximal apices 914, as described. The distal end 904 includes the anchor assemblies including an anchor housing 922A and an embodiment of the anchor 920. In FIG. 9, a distal end 926A of the anchor 920 is shown extending into and through the housing 922A. Rotation of driver 924D at the proximal end of anchor 920 axially translates the anchor 920 through the housing 922A.

The housing 922A is coupled with the distal apexes 916 and receives the anchors 920 therethrough. The collars 918 and anchors 920 are shown in a relative proximal position and may be adjusted proximally or distally therefrom to effect various changes in the frame 910. The implant 900 may have any of the same or similar features and/or functionalities as any other implant described herein, including but not limited to the implant 700 and/or 800 and vice versa.

In FIG. 9 the implant 900 supports a plurality of anchor assemblies, each anchor assembly including an anchor 920 and a housing 922A. The implant 900 may have one or more of the anchor assemblies. As shown there are eight anchor assemblies. There may be one, two, three, four, five, six, seven, nine, ten, eleven, twelve, or more anchor assemblies. There may be one of the anchor assembly for each distal apex 916. The housings 922A of the anchor assemblies are coupled with, for example attached to, the distal end 904 of the implant 900, such as with the corresponding distal apex 916.

The housing 922A may be a separate part that is attached to the frame 910, or the housing 922A maybe integral with the frame 910, such as with the distal apex 916. The housings 922A are located primarily on a radially inward side of the distal apexes 916. The housing 922A may be located entirely on a radially inward side. The housings 922A extend from the apex 916 toward the central longitudinal axis of the implant 900. In some embodiments, the housings 922A may be located primarily or entirely on radially outer sides of the distal apexes 916.

FIGS. 10A through 10E are sequential perspective views of an embodiment of a delivery system 401 with imaging capability showing an embodiment of a method for the delivery, positioning and anchoring of the various implants that may include the restraint described herein, the implant for resizing the native valve annulus. While 10A through 10E depict delivery of an implant 1 for resizing the annulus, it is understood that implants for replacing the valve may also be delivered with the system 401. The implant 1 may be delivered, positioned and anchored to reshape the valve annulus. The implant 1 may be inserted using the delivery system 401 via access to the vasculature of the leg, in particular the femoral vein or the iliac vein. The system 401 may include the various implants, catheters and other features described herein, for example the implant 1, the delivery catheter 240, an intravascular cardiac echography (ICE) catheter ICE catheter 300, the guidewire 306, etc. The system 401 may include any of the implants described herein, for example implants including valve annulus reshaping devices or valve replacements that include valve leaflets. The implant in FIG. 10A may be loaded in the delivery catheter in a compressed state as shown in FIG. 2B.

Figure 10B:
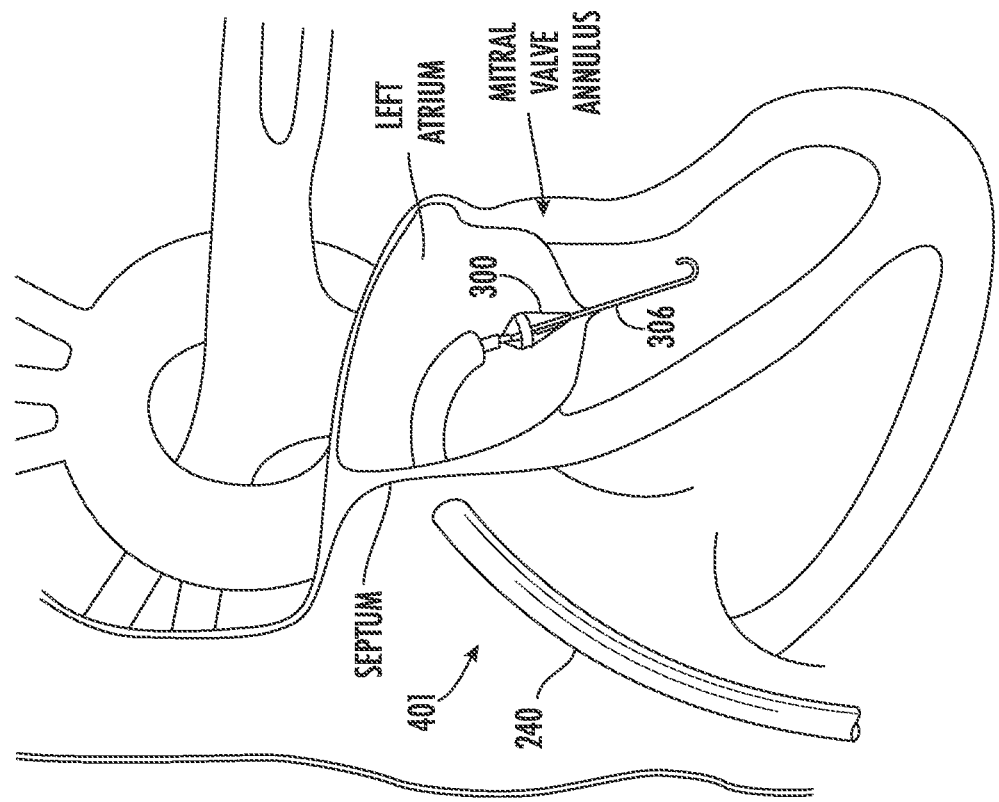
FIGS. 10A through 10E are sequential perspective views of an embodiment of a delivery system with imaging capability showing an embodiment of a method for the delivery, positioning and anchoring of the various implants that may use embodiments of the restraint described herein.
Figure 10A:
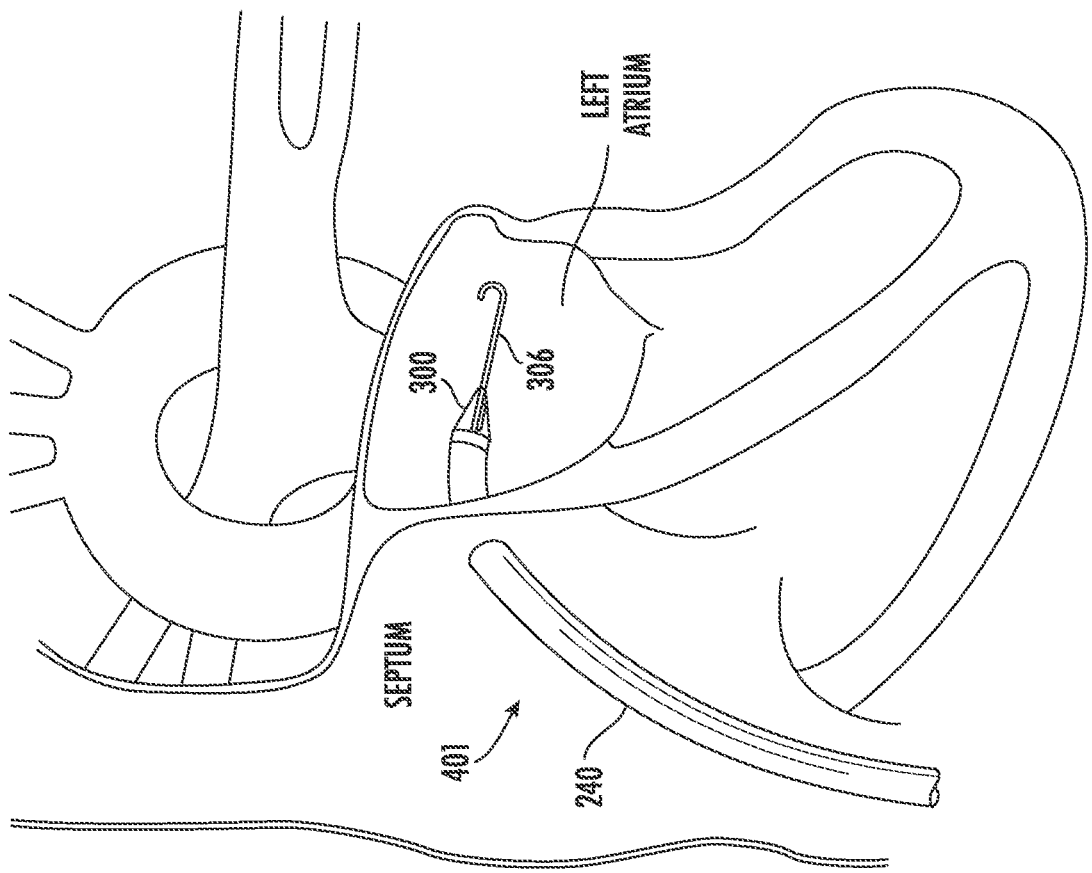
Figure 10D:
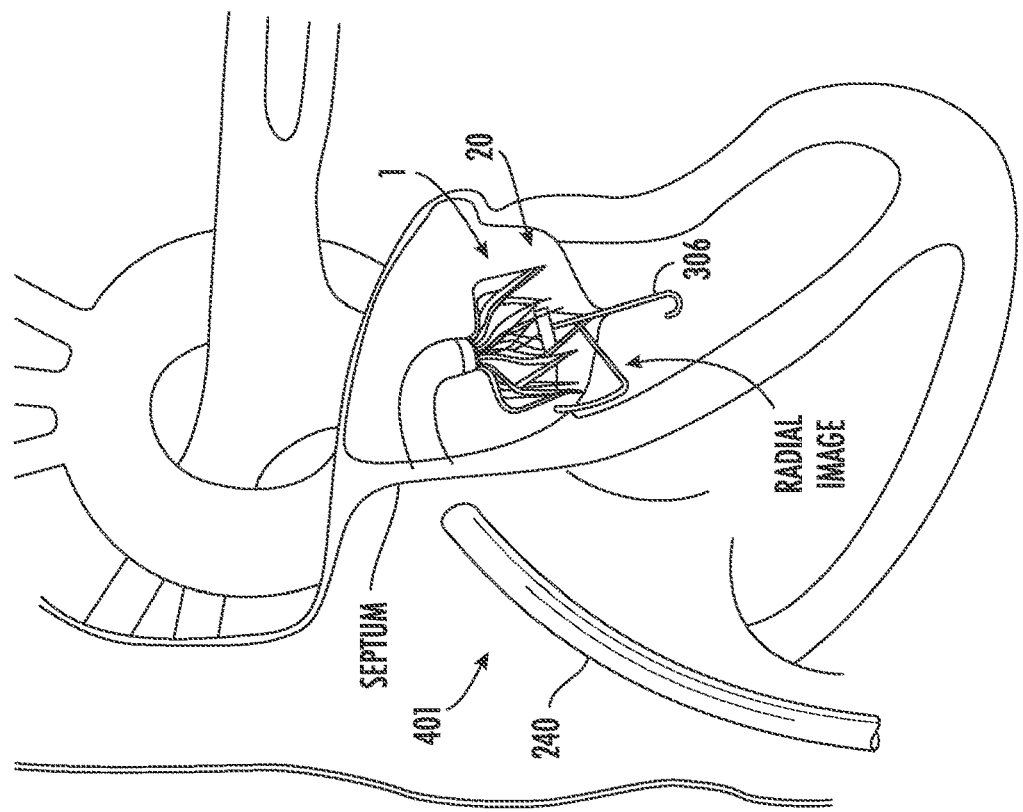
Figure 10C:
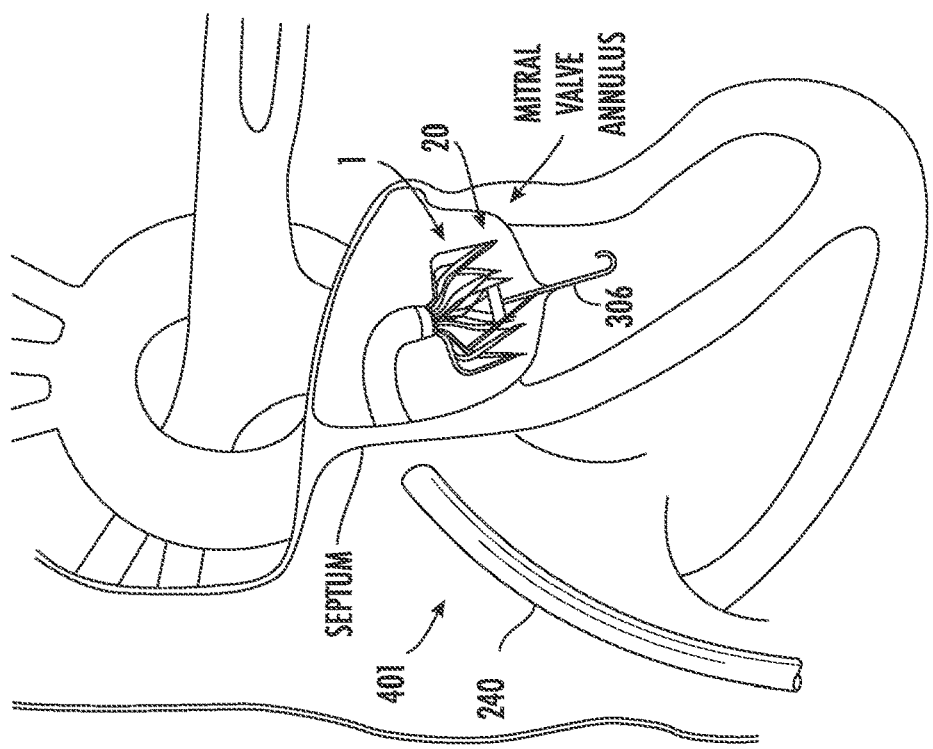
Figure 10E:
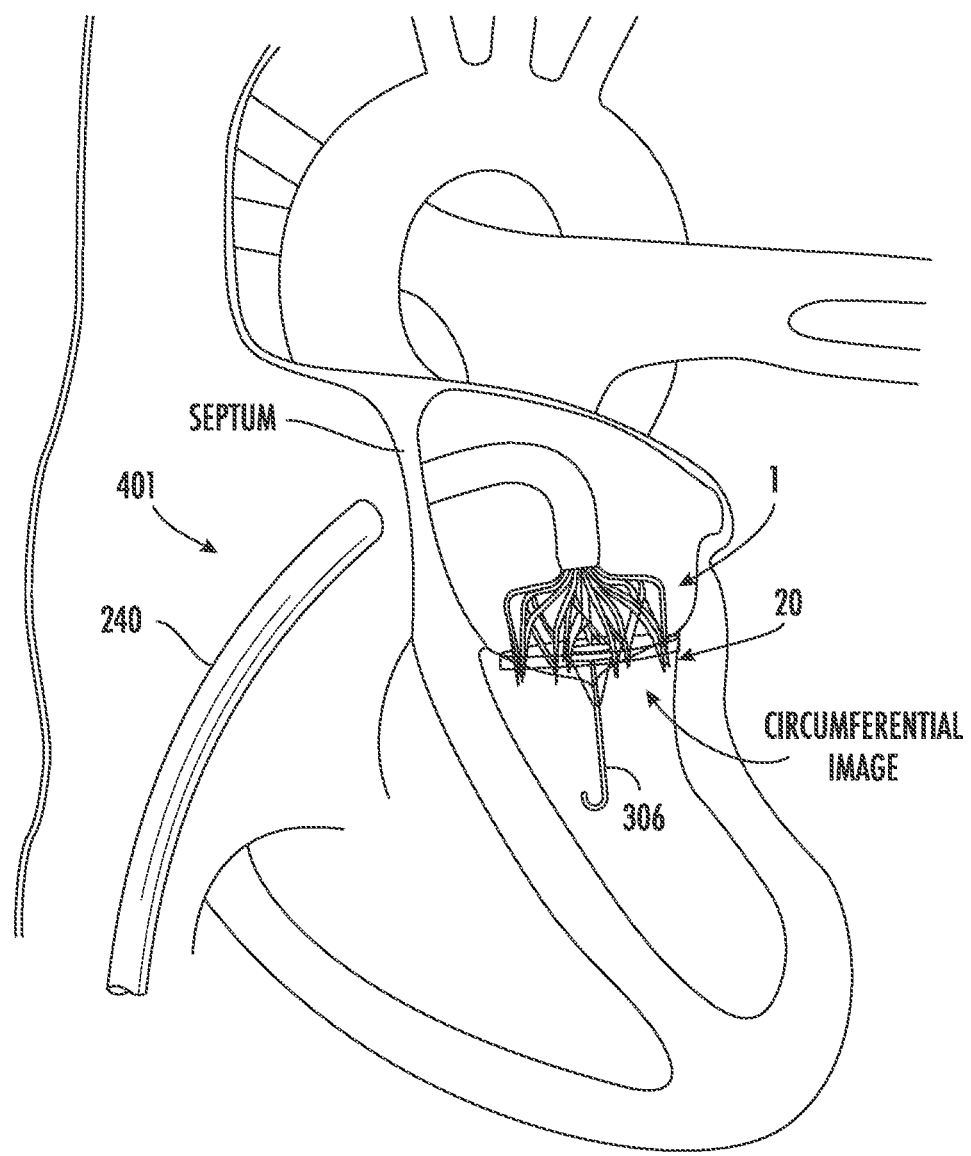

As shown in FIG. 10A, the system 401 is then advanced across the septum separating the upper chambers of the heart. The ICE catheter 300 is advanced to a position above the heart valve annulus, for example, the mitral valve annulus, as shown in FIG. 10B. FIG. 10C shows the implant 1 expelled from the distal end of the delivery system 401 above and proximate to the mitral valve annulus, for example following release of the restraint as described in FIG. 1A. A series of radial images are taken to properly position the anchors 20 for insertion into the mitral valve annulus tissue, as shown in FIG. 10D. Subsequently, a circumferential image is captured, as shown in FIG. 10E, to confirm that all anchors 20 are appropriately placed and anchored in the mitral valve annulus tissue above the mitral valve leaflets. If one or more anchors 20 are not positioned or anchored properly, they can be rotationally retracted, repositioned and re-anchored prior to removal of the driver tubes. In addition, a circumferential image can be taken prior to anchoring to confirm location of the lower crowns 16 of the implant 1. It should also be understood that treatment of the tricuspid valve could involve insertion of the system 401 for access through the jugular vein whereby the system is then advanced down the superior vena cava and into the right atrium proximate and above the tricuspid valve annulus.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A delivery system for an implantable cardiac device, the delivery system comprising:
an implant having a distal end and a proximal end, the implant having a collapsed configuration and an expanded configuration; and
a restraint having a tubular sidewall defining an opening configured to receive a portion of the implant, the tubular sidewall configured to surround the portion of the implant in its collapsed configuration for delivery to an implant site, the tubular sidewall having a plurality of recesses extending longitudinally along an inner surface thereof configured to receive the portion of the implant.

2. The delivery system of claim 1, further comprising:
a delivery catheter having a proximal and a distal end and at least one channel extending therethrough, wherein the implant is positioned proximate the distal end of the delivery catheter and restrained in the collapsed configuration by the restraint; and
a tether connected to the restraint and extending through the at least one channel of the delivery catheter to the proximal end of the delivery catheter, whereby manipulation of the tether causes the restraint to advance distally of the implant and release the implant from the collapsed configuration.

3. The delivery system of claim 1, wherein the plurality of recesses are circumferentially spaced apart.

4. The delivery system of claim 3, wherein the implant comprises a ring-like member having upper apices at its proximal end and lower apices at its distal end, and the restraint is internally recessed to receive the lower apices of the ring-like member when the implant is in the collapsed configuration.

5. The delivery system of claim 1, wherein the restraint has a shaped leading edge to reduce trauma to a patient's anatomy during delivery of the implant.

6. The delivery system of claim 5, wherein the restraint further comprises:
a distal leading section;
a central section; and
a proximal cuff section;
wherein:
a distal section of the restraint is shaped in a rounded manner to reduce trauma to a patient's anatomy; and
the proximal cuff section is shape set so as to taper radially inwardly in a set configuration to aid in retraction through an unrestrained configuration of the implant and into a guide catheter.

7. The delivery system of claim 1, wherein the restraint is configured to surround the distal end of the implant.

8. The delivery system of claim 7, wherein:
the tubular sidewall extends from a proximal end to a distal end;
the opening defined by the tubular sidewall is defined at the proximal end of the tubular sidewall;
the tubular sidewall defines a channel extending distally from the proximal opening; and
the restraint is configured to receive the implant in the collapsed configuration through the proximal opening to radially restrain the implant within the channel.

9. The delivery system of claim 8, wherein the restraint further comprises a distal end wall closing off the distal end of the restraint.

10. The delivery system of claim 1, the implant further comprising:
a tubular frame having a proximal end, a distal end, and a central channel extending therethrough;
the tubular frame comprising a first pair of adjacent struts joined at a proximal apex;
a shaft carried by the proximal apex, the shaft extending along a rotation axis and having an external thread, the shaft configured to rotate about the rotation axis; and
a collar carried by the tubular frame and having an opening extending axially therethrough in which to receive the shaft, the collar having a complementary surface structure for engaging the threads of the shaft, the collar configured to at least partially surround the first pair of adjacent struts;
wherein rotation of the shaft about the rotation axis in a first rotation direction causes the collar to advance along the first pair of struts of the tubular frame to change an angle between the first pair of adjacent struts.

11. The delivery system of claim 10, the implant further comprising an anchor coupled with the tubular frame, the anchor configured to engage tissue of a mitral valve annulus.

12. The delivery system of claim 11, wherein the tubular frame comprises a second pair of adjacent struts joined at a distal apex, wherein the anchor is coupled with the distal apex.

13. A deployment restraint for an implant, the restraint comprising:
a tubular sidewall extending from a proximal end to a distal end;
a proximal opening defined by the tubular sidewall at the proximal end; and
a channel defined by the tubular sidewall and extending distally from the proximal opening and dimensioned to receive the implant;
wherein the restraint includes a plurality of recesses extending longitudinally along an inner surface of the tubular sidewall and configured to receive at least a portion of the implant in a collapsed configuration through the proximal opening to radially restrain the portion of the implant within the channel.

14. The deployment restraint of claim 13, wherein the restraint further comprises a distal end wall closing off the distal end of the restraint.

15. The deployment restraint of claim 13, wherein the implant further comprises:
a tubular frame having a proximal end, a distal end and a central channel extending therethrough, the tubular frame comprising a first pair of adjacent struts joined at a proximal apex;
a shaft carried by the proximal apex, the shaft extending along a rotation axis and having an external thread, the shaft configured to rotate about the rotation axis; and
a collar carried by the tubular frame and having an opening extending axially therethrough in which to receive the shaft, the collar having a complementary surface structure for engaging the threads of the shaft, the collar configured to at least partially surround the first pair of adjacent struts, wherein rotation of the shaft about the rotation axis causes the collar to advance along the first pair of adjacent struts of the tubular frame to change an angle between the first pair of adjacent struts; and an anchor coupled with the tubular frame, the anchor configured to engage tissue of a mitral valve annulus.

16. A method of delivering an implantable cardiac device to a valve annulus, the method comprising:

percutaneously delivering a delivery catheter and an implant to an implant site, wherein the delivery catheter has a proximal end and a distal end and at least one channel extending therethrough, and the implant is positioned proximate the distal end of the delivery catheter, and is surrounded by a tubular restraint, coupled to the delivery catheter by a tether, having a plurality of recesses extending longitudinally along an inner surface thereof and configured to receive a portion of the implant to restrain the portion of the implant in a collapsed configuration; and manipulating one of the implant or the tether to advance the restraint distally of the implant to release the portion of the implant from the collapsed configuration.

17. The method of claim 16, further including proximally retracting the restraint through the implant and delivery catheter.

18. The delivery system of claim 1, wherein the restraint is positioned over only a portion of the implant.

19. The delivery system of claim 1, wherein the restraint restrains the implant in its collapsed configuration as the restraint advances the implant through a delivery catheter.

20. The delivery system of claim 1, further comprising a push wire attached to the restraint and configured to constrain the implant.

* * * * *